(12) United States Patent
Grote

(10) Patent No.: US 9,593,111 B2
(45) Date of Patent: Mar. 14, 2017

(54) OXIDATIVE DEAROMATIZATION OF BERBINES

(71) Applicant: Mallinckrodt LLC, Hazelwood, MO (US)

(72) Inventor: Christopher W. Grote, Hazelwood, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 14/736,752

(22) Filed: Jun. 11, 2015

(65) Prior Publication Data
US 2015/0361076 A1    Dec. 17, 2015

Related U.S. Application Data

(60) Provisional application No. 62/010,648, filed on Jun. 11, 2014.

(51) Int. Cl.
*C07D 471/04* (2006.01)
(52) U.S. Cl.
CPC .................. *C07D 471/04* (2013.01)
(58) Field of Classification Search
None
See application file for complete search history.

(56) References Cited

U.S. PATENT DOCUMENTS

| 4,033,966 A | 7/1977 | Sawa |
| 7,915,276 B2 * | 3/2011 | Kim ..................... C07D 455/03 514/280 |

| 2010/0056789 A1 | 3/2010 | Wang |
| 2012/0308589 A1 | 12/2012 | Yao |
| 2013/0064825 A1 | 3/2013 | Chan |

FOREIGN PATENT DOCUMENTS

| CN | 102850346 | * | 1/2013 |
| WO | 2015/191837 A1 |  | 12/2015 |

OTHER PUBLICATIONS

Mizuta et al., 35(6) Chem. & Pharm. Bull. 2238-42 (1987).*
Hanaoka et al., Chemical Transformation of Protoberberines. XIII. A Novel and Efficient Synthesis of Antitumor Benzo [c] phenanthridine Alkaloids, Nitidine and Fagaronine,: Chem. Pharm. Bull., 1987, pp. 2348-2354, vol. 35(6).
Hanaoka et al., "Chemical Transformation of Protoberberines. VIII. A Novel Synthesis of (±)-Fumaricine and a Formal Synthesis of (±)-Alpinigenine," Chem. Phar, Bull. 1985, pp. 2273-2280, vol. 33(6).
Hanaoka et al., "A New Total Synthesis of Oxyterihanine," Heterocycles, 1987, pp. 1499-1501, vol. 26(6).
Moriarty R. M. and Prakash, O. "Oxidation of Phenolic Compounds with Organohypervalent Iodine Reagents," Organic Reactions, 2001, pp. 327-415, vol. 57, (DOI: 10.1002/0471264180.or057.02).
Reddy, G. C., "Hypervalent iodine oxidation products of papaverine and its microbial metabolites," 1995, Tetrahedron Letters, pp. 1001-1002, vol. 36(7).
International Search Report and Written Opinion issued Sep. 3, 2015 in related International Application No. PCT/US2015/035300, 9 pgs.

* cited by examiner

*Primary Examiner* — Timothy R Rozof

(57) ABSTRACT

The present disclosure provides oxidized berbine derivatives, processes for their preparation, and methods of using the oxidized berbine derivatives.

20 Claims, No Drawings

OXIDATIVE DEAROMATIZATION OF BERBINES

CROSS-REFERENCE TO RELATED APPLICATIONS

This application claims the priority of U.S. Provisional Application Ser. No. 62/010,648, filed Jun. 11, 2014, which is hereby incorporated by reference in its entirety.

FIELD

The present disclosure generally relates to the oxidative dearomatization of berbines and the resultant berbine derivatives.

BACKGROUND

The berbine class of heterocyclic compounds is structurally related to the plant alkaloid berberine. Berbine compounds have been reported to have numerous therapeutic effects. For example, berbines have been found to have antimicrobial, antidiabetic, analgesic, and anticancer activities. Because of the potential therapeutic value of berbine compounds and derivatives thereof, there is a need for new derivatives than may be more potent and/or efficacious.

SUMMARY

Among the various aspects of the present disclosure is the provision of a compound of Formula (VIIIa), Formula (VIIIb), or a pharmaceutically acceptable salt thereof, as diagrammed below:

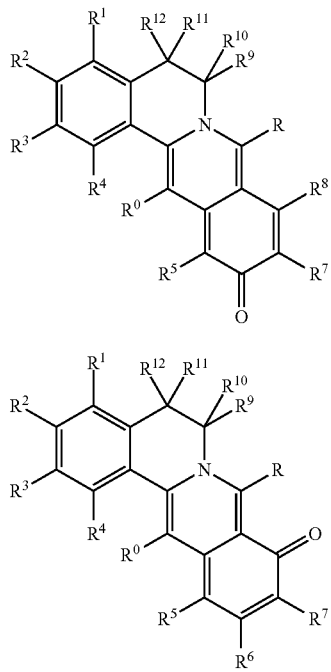

wherein:
R is hydrogen, hydrocarbyl or substituted hydrocarbyl;
$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form $\{-\}O(CH_2)_nO\{-\}$;
$R^5$, $R^6$, when present, $R^7$, and $R^8$, when present, independently are hydrogen, halogen, $OR^{15}$, $NO_2$, $NR^{15}R^{16}$, cyano, thiol, hydrocarbyl, or substituted hydrocarbyl;
$R^0$, $R^9$, $R^{10}$, $R^{11}$, and $R^{12}$ independently are hydrogen, halogen, hydrocarbyl, or substituted hydrocarbyl;
$R^{15}$ and $R^{16}$ independently are hydrogen, hydrocarbyl, or substituted hydrocarbyl; and
n is an integer from 1 to 3.

A further aspect of the present disclosure provides a process for preparing a compound of Formula (VIIIa) or Formula (VIIIb), the process comprising either a) contacting a compound of Formula (VIIa) with an oxidizing agent to form the compound of Formula (VIIIa) according to the following reaction scheme:

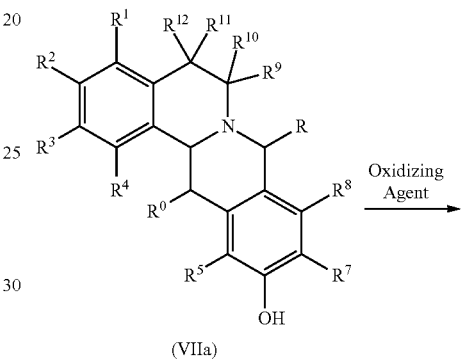

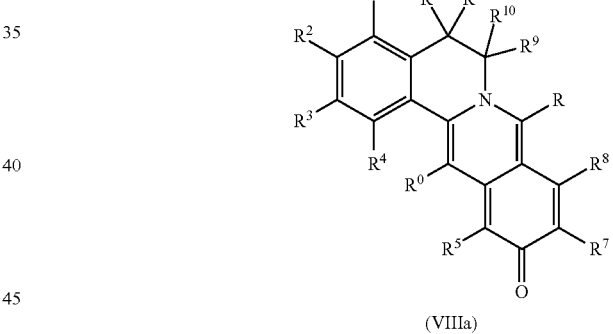

or step b) contacting a compound of Formula (VIIb) with an oxidizing agent to form the compound of Formula (VIIIb) according to the following reaction scheme:

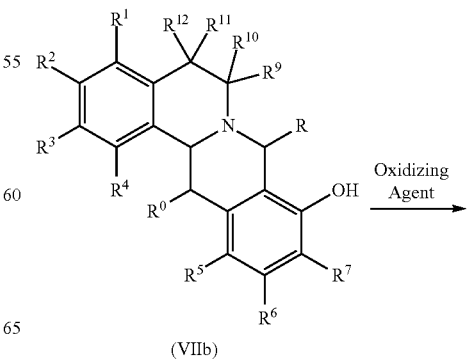

-continued

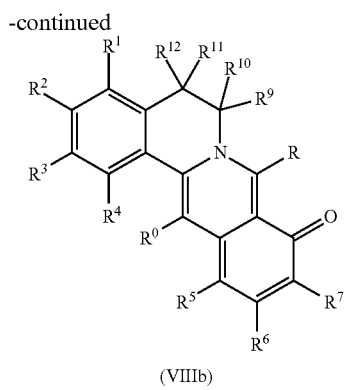

(VIIIb)

wherein:
R is hydrogen, hydrocarbyl or substituted hydrocarbyl;
$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form $\{-\}O(CH_2)_nO\{-\}$;
$R^5$, $R^6$, when present, $R^7$, and $R^8$, when present, independently are hydrogen, halogen, $OR^{15}$, $NO_2$, $NR^{15}R^{16}$, cyano, thiol, hydrocarbyl, or substituted hydrocarbyl;
$R^0$, $R^9$, $R^{10}$, $R^{11}$, and $R^{12}$ independently are hydrogen, halogen, hydrocarbyl, or substituted hydrocarbyl;
$R^{15}$ and $R^{16}$ independently are hydrogen, hydrocarbyl, or substituted hydrocarbyl;
n is an integer from 1 to 3; and
wherein each of $R^1$, $R^2$, $R^3$, $R^4$, $R^5$, $R^6$, when present, $R^7$, and $R^8$, when present, is other than hydroxy.

Still another aspect of the present disclosure encompasses a method for inhibiting the growth of a cancer cell. The method comprises contacting the cancer cell with an effective amount of a compound of Formula (VIIIa), Formula (VIIIb), or a pharmaceutically acceptable salt thereof:

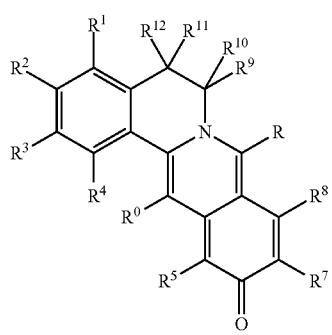

(VIIIa)

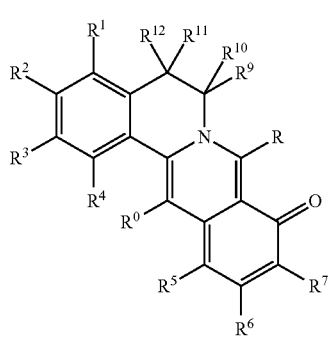

(VIIIb)

wherein:
R is hydrogen, hydrocarbyl or substituted hydrocarbyl;
$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form $\{-\}O(CH_2)_nO\{-\}$;
$R^5$, $R^6$, when present, $R^7$, and $R^8$, when present, independently are hydrogen, halogen, $OR^{15}$, $NO_2$, $NR^{15}R^{16}$, cyano, thiol, hydrocarbyl, or substituted hydrocarbyl;
$R^0$, $R^9$, $R^{10}$, $R^{11}$, and $R^{12}$ independently are hydrogen, halogen, hydrocarbyl, or substituted hydrocarbyl;
$R^{15}$ and $R^{16}$ independently are hydrogen, hydrocarbyl, or substituted hydrocarbyl; and
n is an integer from 1 to 3.

Other aspects and iterations of the disclosure are described in more detail below.

DETAILED DESCRIPTION

The present invention provides berbine derivatives comprising cyclohexadienone moieties and processes for their preparation. The compounds disclosed herein may be used to inhibit the growth of cancer cells.

For ease of discussion, the ring atoms of berbine compounds are numbered as diagrammed below.

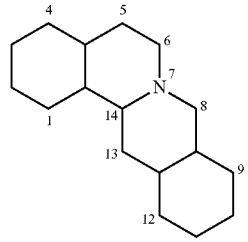 [SMILES: C1CCC2CN3CCC4CCCCC4C3CC2C1]

(I) Oxidized Berbine Compounds
(a) Compounds of Formula (VIIIa)
One aspect of the present disclosure encompasses compounds having Formula (VIIIa):

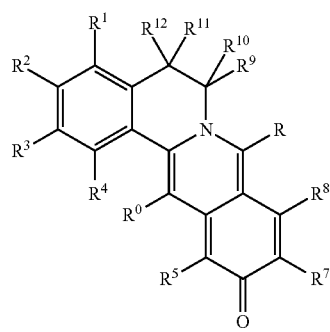

(VIIIa)

wherein:
R is hydrogen, hydrocarbyl or substituted hydrocarbyl;
$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form $\{-\}O(CH_2)_nO\{-\}$;
$R^5$, $R^7$, and $R^8$ independently are hydrogen, halogen, $OR^{15}$, $NO_2$, $NR^{15}R^{16}$, cyano, thiol, hydrocarbyl, or substituted hydrocarbyl;

$R^0$, $R^9$, $R^{10}$, $R^{11}$, and $R^{12}$ independently are hydrogen, halogen, hydrocarbyl, or substituted hydrocarbyl;

$R^{15}$ and $R^{16}$ independently are hydrogen, hydrocarbyl, or substituted hydrocarbyl; and n is an integer from 1 to 3.

In various embodiments, R may be hydrogen, alkyl, substituted alkyl, alkenyl, substituted alkenyl, aryl, or substituted aryl. In some iterations, R may be hydrogen. In other iterations, R may be lower alkyl, which is defined herein as $C_1$-$C_6$. The alkyl may be linear, branched, or cyclic, and optionally substituted. For example, R may be methyl, ethyl, propyl, cyclopropyl, cyclobutyl, cyclopentyl, cyclohexyl, morpholinyl, piperidinyl, piperazinyl, or any of the foregoing substituted with amino, alkyl, alkoxy, halogen, hydroxy, nitro, or oxo. In further iterations, R may be aryl or substituted aryl. For example, R may be phenyl, benzyl, pyrazolyl, imidazolyl, pyrazinyl, oxazinyl, or any of the foregoing substituted with amino, alkyl, alkoxy, halogen, hydroxy, nitro, or oxo.

In some embodiments, $R^{15}$ and $R^{16}$ independently may be hydrogen, alkyl, substituted alkyl, alkenyl, substituted alkenyl, aryl, or substituted aryl. In certain iterations, $R^{15}$ and $R^{16}$ independently may be hydrogen, $C_1$-$C_6$ alkyl, acyl (i.e., C(=O)R, wherein R is alkyl or aryl), phenyl, or substituted versions thereof.

In certain embodiments, $R^1$, $R^2$, $R^3$, and $R^4$ independently may be hydrogen, halogen, hydroxy, $C_1$-$C_6$ alkoxy, aryloxy, amine, amino, or nitro, or together $R^2$ and $R^3$ may form {—}O(CH$_2$)$_n$O{—}, wherein n is 1 or 2. In certain iterations, each of $R^1$ and $R^4$ may be hydrogen, and $R^2$ and $R^3$ independently may be hydrogen, hydroxy, or $C_1$-$C_6$ alkoxy, or together $R^2$ and $R^3$ may form {—}O(CH$_2$)$_n$O{—}, wherein n is 1. In one aspect, each of $R^1$, $R^3$, and $R^4$ may be hydrogen, and $R^2$ may be hydroxy or methoxy. In another aspect, each of $R^1$ and $R^4$ may be hydrogen, and together $R^2$ and $R^3$ may form {—}O(CH$_2$)O{—}.

In various embodiments, $R^0$, $R^9$, $R^{10}$, $R^{11}$, and $R^{12}$ independently may be hydrogen, halogen, alkyl, substituted alkyl, alkenyl, substituted alkenyl, aryl, or substituted aryl. In specific embodiments, each of $R^0$, $R^9$, $R^{10}$, $R^{11}$, and $R^{12}$ may be hydrogen.

In some embodiments, $R^5$, $R^7$, and $R^8$ independently may be hydrogen, halogen, hydroxy, $C_1$-$C_6$ alkoxy, aryloxy, amine, amino, or nitro. In some iterations, $R^5$ and $R^8$ may be hydrogen and $R^7$ may be hydroxy or $C_1$-$C_6$ alkoxy. In other iterations, $R^5$ may be halogen, $R^7$ may be hydroxy or $C_1$-$C_6$ alkoxy, and $R^8$ may be hydrogen.

In specific embodiments, R may be hydrogen, alkyl, substituted alkyl, cycloalkyl, substituted cycloalkyl, aryl, or substituted aryl; each of $R^0$, $R^1$, $R^4$, $R^9$, $R^{10}$, $R^{11}$, and $R^{12}$ may be hydrogen; $R^2$ may be hydroxy or $C_1$-$C_6$ alkoxy and $R^3$ may be hydrogen, or together $R^2$ and $R^3$ may form {—}O(CH$_2$)O{—}; $R^5$ may be hydrogen or halogen; $R^7$ may be hydroxy or $C_1$-$C_6$ alkoxy; and $R^8$ may be hydrogen.

Specific examples of compounds of Formula (VIIIa) are shown below:

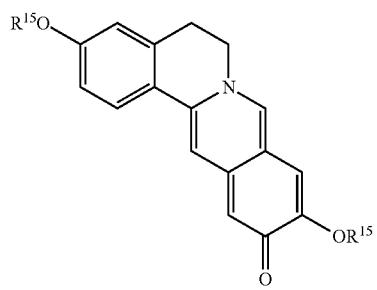

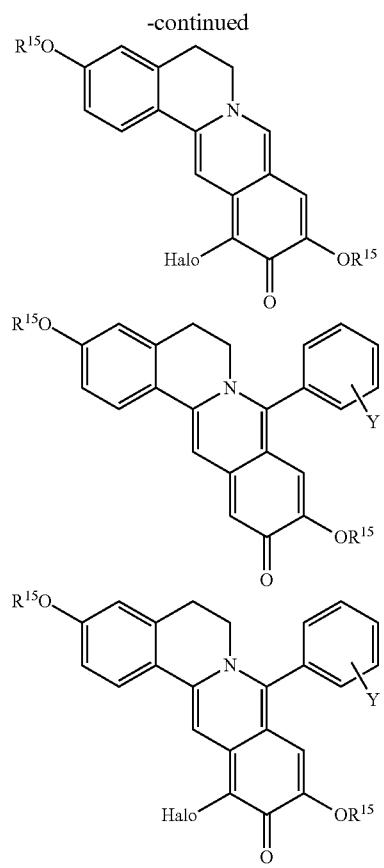

wherein $R^{15}$ is hydrogen or $C_1$-$C_6$ alkyl, and Y is hydrogen, amino, $C_1$-$C_6$ alkyl, $C_1$-$C_6$ alkoxy, halogen, hydroxy, or nitro.

(b) Compounds of Formula (VIIIb)

Another aspect of the present disclosure provides compounds of Formula (VIIIb):

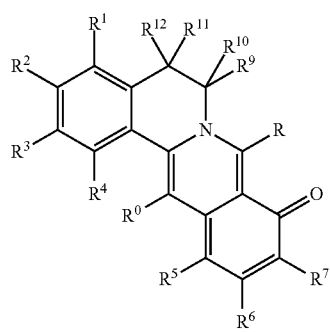

(VIIIb)

wherein:
R is hydrogen, hydrocarbyl or substituted hydrocarbyl;
$R^1$, $R^2$, $R^3$, and $R^4$ independently are hydrogen, halogen, OR$^{15}$, NO$_2$, NR$^{15}$R$^{16}$, cyano, thiol, hydrocarbyl, substituted hydrocarbyl, or together $R^2$ and $R^3$ form {—}O(CH$_2$)$_n$O{—};
$R^5$, $R^6$, and $R^7$ independently are hydrogen, halogen, OR$^{15}$, NO$_2$, NR$^{15}$R$^{16}$, cyano, thiol, hydrocarbyl, or substituted hydrocarbyl;
$R^0$, $R^9$, $R^{10}$, $R^{11}$, and $R^{12}$ independently are hydrogen, halogen, hydrocarbyl, or substituted hydrocarbyl;

$R^{15}$ and $R^{16}$ independently are hydrogen, hydrocarbyl, or substituted hydrocarbyl; and n is an integer from 1 to 3.

In various embodiments, R may be hydrogen, alkyl, substituted alkyl, alkenyl, substituted alkenyl, aryl, or substituted aryl. In some iterations, R may be hydrogen. In other iterations, R may be lower alkyl, which is defined herein as $C_1$-$C_6$. The alkyl may be linear, branched, or cyclic, and optionally substituted. For example, R may be methyl, ethyl, propyl, cyclopropyl, cyclobutyl, cyclopentyl, cyclohexyl, morpholinyl, piperidinyl, piperazinyl, or any of the foregoing substituted with amino, alkyl, alkoxy, halogen, hydroxy, nitro, or oxo. In further iterations, R may be aryl or substituted aryl. For example, R may be phenyl, benzyl, pyrazolyl, imidazolyl, pyrazinyl, oxazinyl, or any of the foregoing substituted with amino, alkyl, alkoxy, halogen, hydroxy, nitro, or oxo.

In some embodiments, $R^{15}$ and $R^{16}$ independently may be hydrogen, alkyl, substituted alkyl, alkenyl, substituted alkenyl, aryl, or substituted aryl. In certain iterations, $R^{15}$ and $R^{16}$ independently may be hydrogen, $C_1$-$C_6$ alkyl, acyl (i.e., C(=O)R, wherein R is alkyl or aryl), phenyl, or substituted versions thereof.

In certain embodiments, $R^1$, $R^2$, $R^3$, and $R^4$ independently may be hydrogen, halogen, hydroxy, $C_1$-$C_6$ alkoxy, aryloxy, amine, amino, or nitro, or together $R^2$ and $R^3$ may form {—}O(CH$_2$)$_n$O{—}, wherein n is 1 or 2. In certain iterations, each of $R^1$ and $R^4$ may be hydrogen, and $R^2$ and $R^3$ independently may be hydrogen, hydroxy, or $C_1$-$C_6$ alkoxy, or together $R^2$ and $R^3$ may form {—}O(CH$_2$)$_n$O{—}, wherein n is 1. In one aspect, each of $R^1$, $R^3$, and $R^4$ may be hydrogen, and $R^2$ may be hydroxy or methoxy. In another aspect, each of $R^1$ and $R^4$ may be hydrogen, and together $R^2$ and $R^3$ may form {—}O(CH$_2$)O{—}.

In various embodiments, $R^0$, $R^9$, $R^{10}$, $R^{11}$, and $R^{12}$ independently may be hydrogen, halogen, alkyl, substituted alkyl, alkenyl, substituted alkenyl, aryl, or substituted aryl. In specific embodiments, each of $R^0$, $R^9$, $R^{10}$, $R^{11}$, and $R^{12}$ may be hydrogen.

In some embodiments, $R^5$, $R^6$, and $R^7$ independently may be hydrogen, halogen, hydroxy, $C_1$-$C_6$ alkoxy, aryloxy, amine, amino, or nitro. In some iterations, $R^5$ and $R^6$ may be hydrogen and $R^7$ may be hydroxy or $C_1$-$C_6$ alkoxy. In other iterations, $R^5$ may be halogen, $R^6$ may be hydrogen, and $R^7$ may be hydroxy or $C_1$-$C_6$ alkoxy.

In specific embodiments, R may be hydrogen, alkyl, substituted alkyl, cycloalkyl, substituted cycloalkyl, aryl, or substituted aryl; each of $R^0$, $R^1$, $R^4$, $R^9$, $R^{10}$, $R^{11}$, and $R^{12}$ may be hydrogen; $R^2$ may be hydroxy or $C_1$-$C_6$ alkoxy and $R^3$ may be hydrogen, or together $R^2$ and $R^3$ may form {—}O(CH$_2$)O{—}; $R^5$ may be hydrogen or halogen; $R^6$ may be hydrogen; and $R^7$ may be hydroxy or $C_1$-$C_6$ alkoxy.

Specific examples of compounds of Formula (VIIIb) are shown below:

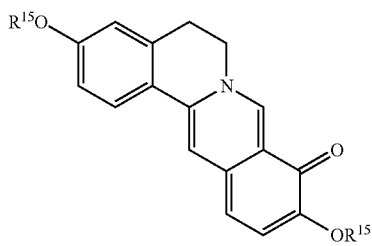

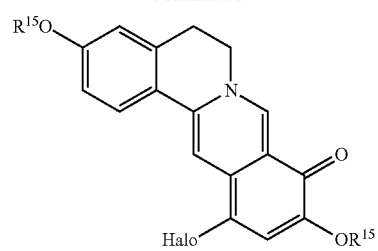

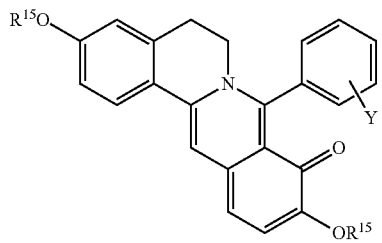

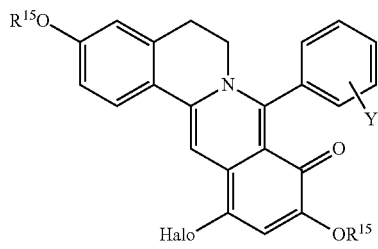

wherein $R^{15}$ is hydrogen or $C_1$-$C_6$ alkyl, and Y is hydrogen, amino, $C_1$-$C_6$ alkyl, $C_1$-$C_6$ alkoxy, halogen, hydroxy, or nitro.

(II) Processes for Preparing Compounds of Formula (VIIIa) or (VIIIb)

Another aspect of the present disclosure provides processes for preparing the compounds disclosed herein. In general, the process entails an oxidative dearomatization reaction in which a phenol moiety is converted to a cyclohexadienone moiety. In particular, the process comprises contacting a compound of Formula (VIIa) or (VIIb) with an oxidizing agent to form a compound of Formula (VIIIa) or (VIIIb), respectively. Reaction Schemes 1 and 2 depict the synthesis of compounds of Formula (VIIIa) or (VIIIb), respectively, in accordance with this aspect of the disclosure:

Reaction Scheme 1:

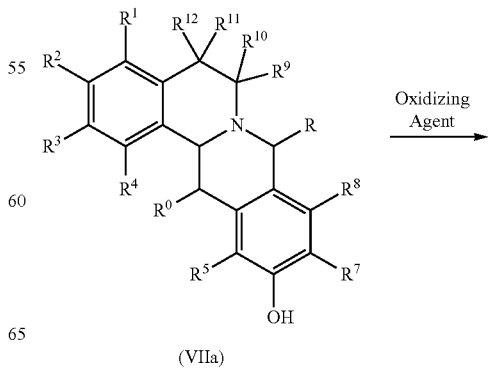

(VIIa)

-continued

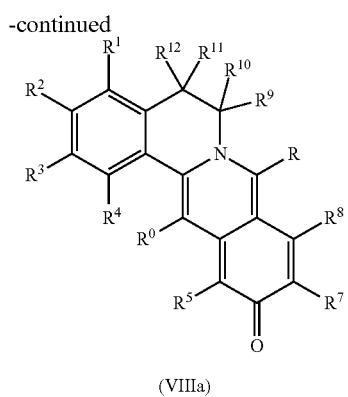

(VIIIa)

Reaction Scheme 2:

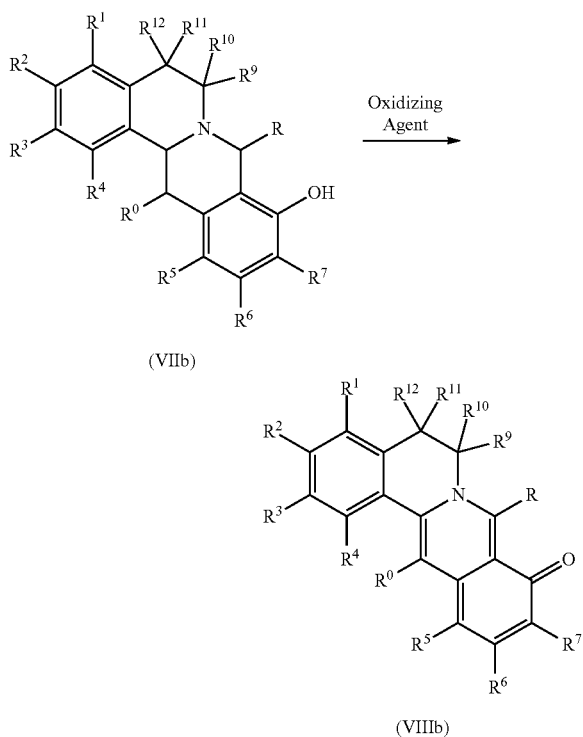

wherein R, $R^0$—$R^{12}$ are as defined above, provided however, that each of $R^1$, $R^2$, $R^3$, $R^4$, $R^5$, $R^6$, when present, $R^7$, and $R^8$, when present, is other than hydroxy.

The process disclosed herein converts a chiral compound into an achiral compound. In particular, the compounds of Formula (VIIa) or (VIIb) generally contain at least one chiral carbon (e.g., C-14).

(a) Reaction Mixture

The process commences with the formation of a reaction mixture comprising a compound having Formula (VIIIa) or (VIIIb) and an oxidizing agent. Generally, the reaction mixture also comprises a solvent. In some embodiments, the reaction mixture may further comprise a proton acceptor.

(i) Oxidizing Agent

A variety of oxidizing agents are suitable for use in the process disclosed herein. Non-limiting examples of suitable oxidizing agents include halogens such as iodine, bromine, and chlorine; quinones such as 2,3-dichloro-5,6-dicyano-p-benzoquinone (DDQ), 1,4-benzoquinone, and chloranil; succinimides such as N-bromosuccinimide, N-chlorosuccinimide, N-iodosuccinimide; chloroisocyanuric acids such as dichloroisocyanuric acid or trichloroisocyanuric acid; and inorganic agents such as silver, cerium (e.g., cerium ammonium nitrate), chromium, copper, molybdenum, selenium, and cobalt. Without being bound by any specific theory, it appears that some oxygen-containing agents such as peroxides and peroxyacids yield N-oxide compounds rather than compounds having Formula (VIIIa) or (VIIIb). In one specific embodiment, the oxidizing agent may be a halogen such as iodine. In another specific embodiment, the oxidizing agent may be a quinone such as DDQ.

The amount of oxidizing agent added to the reaction mixture can and will vary depending upon, for example, the strength of the oxidizing agent. In general, the mole to mole ratio of the compound of Formula (VIIa) or (VIIb) to the oxidizing agent may range from about 1:1 to about 1:10. In various embodiments, the mole to mole ratio of the compound of Formula (VIIa) or (VIIb) to the oxidizing agent may range about 1:1 to about 1:2, from about 1:2 to about 1:4, from about 1:4 to about 1:6, from about 1:6 to about 1:8, or from about 1:8 to about 1:10. In one embodiment, the mole to mole ratio of the compound of Formula (VIIa) or (VIIb) to the oxidizing agent may be about 1:1.5. In another embodiment, the mole to mole ratio of the compound of Formula (VIIa) or (VIIb) to the oxidizing agent may be about 1:2. In a further embodiment, the mole to mole ratio of the compound of Formula (VIIa) or (VIIb) to the oxidizing agent may be about 1:4.

(ii) Solvent

The reaction mixture generally further comprises a solvent. In general, the solvent is a non-oxidizable solvent. Non-limiting examples of suitable solvents include alcohols (e.g., ethanol, methanol, isopropanol, etc.), acetonitrile, N,N-dimethylformamide, N,N-dimethylacetamide, tetrahydrofuran, chloroform, dichloromethane, dichloroethane, chloromethane, benzene, chlorobenzene, fluorobenzene, heptane, hexane, cyclohexane, toluene, hexamethylphosphoramide, acetamide, benzamide, 2-methyl tetrahydrofuran, tetrahydropyran, propionitrile, propylene glycol, ethylene glycol, propanediol, and combinations thereof. In one specific embodiment, the solvent may be ethanol. In another specific embodiment, the solvent may be acetonitrile.

In general, the volume to mass ratio (i.e., mL per g) of the solvent to the compound of Formula (VIIa) or (VIIb) ranges from about 10:1 to about 300:1. In various embodiments, the volume to mass ratio of the solvent to the compound of Formula (VIIa) or (VIIb) may range from 10:1 to about 50:1, from about 50:1 to about 100:1, from about 100:1 to about 200:1, or from about 200:1 to about 300:1. In specific embodiments, the volume to mass ratio of the solvent to the compound of Formula (VIIa) or (VIIb) may range from about 50:1 to about 250:1.

(iii) Optional Proton Acceptor

In some embodiments, the reaction mixture may further comprise a proton acceptor. Non-limiting examples of suitable proton acceptors include acetate salts (such as potassium acetate, sodium acetate, and the like), bicarbonate salts (such as lithium bicarbonate, potassium bicarbonate, sodium bicarbonate and so forth), borate salts (such as potassium borate, sodium borate, etc.), carbonate salts (such as calcium carbonate, lithium carbonate, potassium carbonate, sodium carbonate, and the like), hydroxide salts (such as calcium hydroxide, potassium hydroxide, sodium hydroxide, and so forth), phosphate salts (such as dipotassium hydrogen phosphate, tripotassium phosphate, disodium hydrogen phosphate, trisodium phosphate, and so forth), butoxides (such as sodium tert-butoxide, potassium tert-butoxide, and the like), organic bases (such as pyridine, triethylamine, diisopropylethylamine, N-methylmorpholine, N,N-dimethylaminopyridine, and so forth), and mixtures of any of the foregoing. In one specific embodiment, the proton acceptor may be sodium acetate.

The amount of proton acceptor added to the reaction mixture can and will vary depending, for example, on the identity of the proton acceptor. In general, the mole to mole ratio of the compound of Formula (VIIa) or (VIIb) to the proton acceptor may range from about 1:1 to about 1:10. In various embodiments, the mole to mole ratio of the compound of Formula (VIIa) or (VIIb) to the proton acceptor may range about 1:1 to about 1:2, from about 1:2 to about 1:4, from about 1:4 to about 1:6, from about 1:6 to about 1:8, or from about 1:8 to about 1:10. In one specific embodiment, the mole to mole ratio of the compound of Formula (VIIa) or (VIIb) to the proton acceptor may range from about 1:3 to about 1:7.

(b) Reaction Conditions

In general, the reaction is conducted at a temperature that ranges from about −50° C. to about 200° C. In various embodiments, the reaction may be conducted at a temperature from about −50° C. to about 0° C., from about 0° C. to about 30° C., from about 30° C. to about 60° C., from about 60° C. to about 100° C., from about 100° C. to about 150° C., or from about 150° C. to about 200° C. In specific embodiments, the reaction may be conducted under reflux. In other embodiments, the reaction may be conducted at room temperature. In further embodiments, the reaction may be conducted at a first temperature and then a second temperature. The reaction generally is performed under ambient pressure.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of the compound of Formula (VIIa) or (VIIb), and a significantly increased amount of the compound of Formula (VIIIa) or (VIIIb) compared to the amounts of each present at the beginning of the reaction. Typically, the amount of the compound of Formula (VIIa) or (VIIb) remaining in the reaction mixture after the reaction is complete may be less than about 3%, or less than about 1%. In general, the reaction may proceed for about 2 hours to about 120 hours. In certain embodiments, the reaction may be allowed to proceed for a period of time ranging from about 2 hours to about 20 hours, from about 20 hours to about 40 hours, from about 40 hours to about 90 hours, from about 90 hours to about 120 hours, or longer than about 120 hours.

The compound of Formula (VIIIa) or (VIIIb) may be isolated from the reaction mixture using techniques known to those of skill in the art. Non-limiting examples of suitable techniques include precipitation, filtration, extraction, evaporation, distillation, chromatography, and crystallization.

The yield of the compound of Formula (VIIIa) or (VIIIb) can and will vary. Typically, the yield of the compound of Formula (VIIIa) or (VIIIb) may be at least about 30% by weight. In certain embodiments, the yield of the compound of Formula (VIIIa) or (VIIIb) may be at least about 40%, at least about 50%, at least about 60%, at least about 70%, at least about 80%, at least about 90%, or at least about 95% by weight.

The compound of Formula (VIIIa) or (VIIIb) may undergo further reactions to form derivatives of the oxidized berbine compounds.

The compounds disclosed herein also may be converted to pharmaceutically acceptable salts. The term "pharmaceutically acceptable salts" refers to salts commonly used to form alkali metal salts or addition salts of free acids or free bases. The nature of the salt may vary, provided that it is pharmaceutically acceptable. Suitable pharmaceutically acceptable acid addition salts of compounds disclosed herein may be prepared from inorganic acids or organic acids. Non-limiting examples of suitable inorganic acids include hydrochloric, hydrobromic, hydroiodic, nitric, carbonic, sulfuric, perchloric, and phosphoric acid. Appropriate organic acids may be selected from aliphatic, cycloaliphatic, aromatic, araliphatic, heterocyclic, carboxylic and sulfonic classes of organic acids, examples of which are formic, acetic, oxalic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts of compounds disclosed herein include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine), and procaine. All of these salts may be prepared by conventional means from the corresponding compound by reacting, for example, the appropriate acid or base with the any of the compounds disclosed herein.

(III) Compositions

A further aspect of the present disclosure encompasses pharmaceutical compositions comprising compounds of Formula (VIIIa), Formula (VIIIb), or a pharmaceutically acceptable salt thereof, which are detailed above in section (I), and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may comprise at least one diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The compositions can be formulated into various dosage forms and administered by a number of different means that will deliver a therapeutically effective amount of the active ingredient (i.e., the compound of Formula (VIIIa) or (VIIIb)). Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, geltabs, caplets, gelcaps, pills, powders, pellets, and granules. In such solid dosage forms, the active ingredient is ordinarily combined with one or more pharmaceutically acceptable excipient, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as ethylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

(IV) Methods of Using

A further aspect of the present disclosure provides methods of using the compound disclosed herein for inhibiting the growth of cancer cells. The method comprises contacting a cancer cell with an effective amount of a compound of Formula (VIIIa), (VIIIb), or a pharmaceutically acceptable salt of either.

The compounds of Formula (VIIIa) or (VIIIb) are detailed above in section (I), and compositions comprising said compounds are described above in section (III).

The method comprises contacting a cancer cell with an effective amount of one of the compounds listed above. The type of cell that is contacted with the compound can and will vary. In some embodiments, the cancer cell may be in vitro. The cancer cell may be a primary cancer cell or a cultured cancer cell line cell. The cancer cell line may be a human cancer cell line or a mammalian cancer cell line. Human or other mammalian cancer cell lines are commercially available and/or are well known to those skilled in the art. The in vitro cancer cell may be contacted with the compound of Formula (VIIIa) or (VIIIb) continuously, for a short period of time, intermittently, or any of a variety of regimes.

In other embodiments, the cancer cell may be in vivo, i.e., the cancer cell may be disposed in a subject. In some embodiments, the subject may be a human. In other embodiments, the subject may be a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

The cancer in the subject may be primary or metastatic; the tumor may be malignant or benign. The cancer may be early stage or late stage. Non-limiting examples of cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

In embodiments in which the cancer cell is in vivo, the cancer cell generally is contacted with the compound by administering an effective amount of the compound of Formula (VIIIa) or (VIIIb) to the subject. The compound may be administered orally (as a solid or a liquid), parenterally (which includes intramuscular, intravenous, intradermal, intraperitoneal, and subcutaneous), or topically (which includes transmucosal and transdermal). An "effective" amount refers to the dose of the compound that inhibits the growth of the cancer cell. The amount to be used can be determined by the skilled practitioner in view of desired dosages and side effects of the compound. The compound of Formula (VIIIa) or (VIIIb) may be administered once or repeatedly to the subject. Repeated administrations may be at regular intervals of 2 hours, 6 hours, 12 hours, 24 hours, 2 days, 5 days, 7 days, 30 days, and so forth.

Following contact with the compound, the growth of the cancer cell generally is inhibited. In some embodiments, cancer cell growth may be inhibited about 0.5-fold, about 1-fold, about 2-fold, about 5-fold, about 10-fold, or more than 10-fold. In other embodiments, cancer cell growth may be inhibited to such a degree that the cell undergoes cell death (via apoptosis or necrosis).

In certain embodiments, the method may further comprise administering at least one chemotherapeutic agent and/or a radiotherapeutic agent. The chemotherapeutic agent and/or radiotherapeutic agent may be administered concurrently or sequentially.

The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, triethylenephosphoramide, triethylenethiophosphaoramide, tri methylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1 BB ligand, and Apo-1 ligand. Also included are pharmaceutically acceptable salts, acids, or derivatives of any of the above listed agents. The mode of administration of the chemotherapeutic agent can and will vary depending upon the agent and the type of cancer. A skilled practitioner will be able to determine the appropriate dose of the chemotherapeutic agent.

The radiotherapeutic agent may include a radioisotope. Suitable radioisotopes include, without limit, Iodine-131, Iodine-125, Iodine-124, Lutecium-177, Phosphorous-132, Rhenium-186, Strontium-89, Yttrium-90, Iridium-192, and Samarium-153. Alternatively, the radiotherapeutic agent may include a high Z-element chosen from gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. The appropriate dose of the radiotherapeutic agent can be determined by a skilled practitioner.

Definitions

Compounds useful in the compositions and processes include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (0), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denotes optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

Having described the invention in detail, it will be apparent that modifications and variations are possible without departing from the scope of the invention defined in the appended claims.

EXAMPLES

Example 1

Oxidation Dearomatization—Trial 1

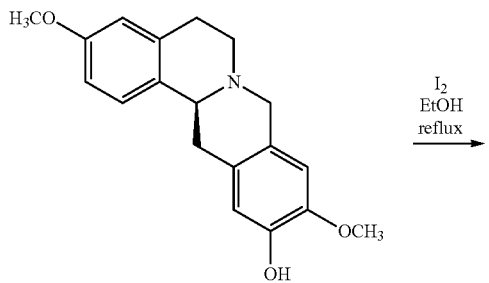

Chemical Formula: $C_{19}H_{21}NO_3$
Exact Mass: 311.15
Molecular Weight: 311.38

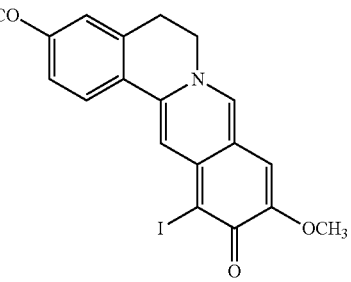

Chemical Formula: $C_{19}H_{16}INO_3$
Exact Mass: 433.02
Molecular Weight: 433.25

Into a 3 necked round bottom flask was charged the berbine (320 mg, 1.027 mmol) and ethanol (25 mL). After stirring for 5 minutes, iodine (4.0 eq., 1.04 g, 4.11 mmol) was introduced into the reactor. The mixture was refluxed for 24 hr and then cooled to room temperature. After stirring at room temperature, a yellow precipitate formed. The solid was filtered, washed with absolute ethanol (10 mL) and was dried overnight under vacuum yielding the product (420 mg, 94% yield) as a yellow solid.

Example 2

Oxidation Dearomatization—Trial 2

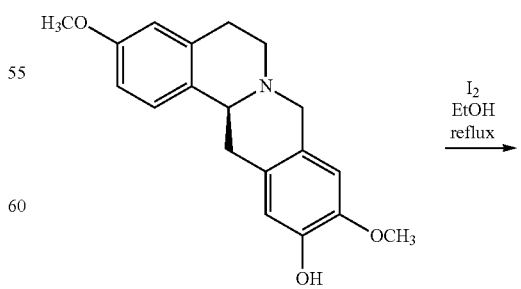

Chemical Formula: $C_{19}H_{21}NO_3$
Exact Mass: 311.15
Molecular Weight: 311.38

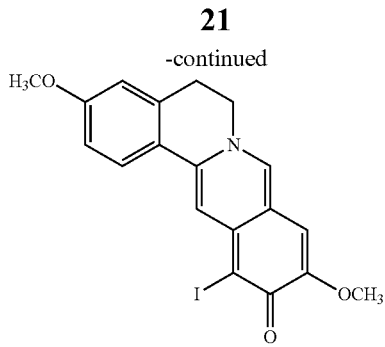

Chemical Formula: C₁₉H₁₆INO₃
Exact Mass: 433.02
Molecular Weight: 433.25

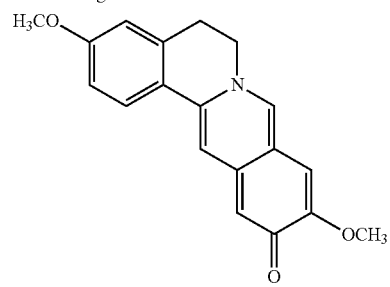

Chemical Formula: C₁₉H₁₇NO₃
Exact Mass: 307.12
Molecular Weight: 307.35

Into a 3 necked round bottom flask was charged the berbine (100 mg, 0.32 mmol) and absolute ethanol (20 mL). Into the reaction mixture was added iodine (4.0 eq., 326 mg, 1.28 mmol). The reaction mixture was refluxed for 48 hr and then cooled to room temperature wherein a precipitate formed. The precipitate was filtered off and then washed with absolute ethanol (5.0 mL). The solid was dissolved in CHCl₃ (50 mL) and then washed with 10% aqueous sodium thiosulfate (20 mL). After drying the chloroform extract with anhydrous Na₂SO₄, filtering, concentrating, and drying overnight under vacuum at 40° C., the product was isolated as a mixture of products (100 mg, 10% MW: 433, 90% MW: 307).

Example 3

Oxidation Dearomatization—Trial 3

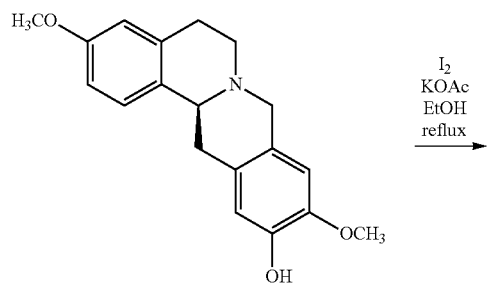

Chemical Formula: C₁₉H₂₁NO₃
Exact Mass: 311.15
Molecular Weight: 311.38

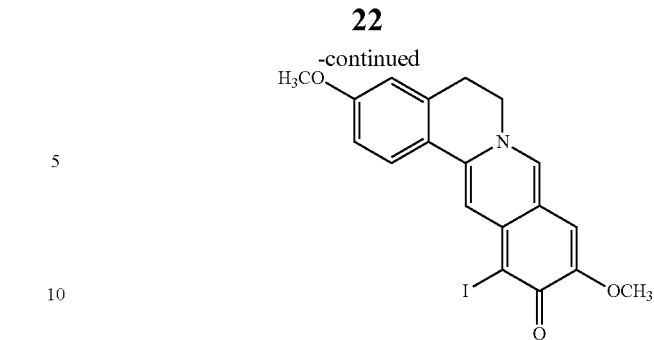

Chemical Formula: C₁₉H₁₆INO₃
Exact Mass: 433.02
Molecular Weight: 433.25

Into a 3 necked round bottom flask was charged the berbine (200 mg, 0.64 mmol), potassium acetate (6.0 eq., 980 mg, 3.85 mmol) and absolute ethanol (50 mL). Into the reaction mixture was added iodine (10.0 eq., 630 mg, 6.40 mmol). The reaction mixture was refluxed for 24 hr and then cooled to room temperature for 48 hr. A dark solid was present on the bottom of the flask. After decanting off the reaction solvent, the dark residue in the bottom of the flask was dissolved in CHCl₃ (100 mL). The chloroform solution was washed with distilled water (50 mL), 10% aqueous sodium thiosulfate (2×25 mL), and saturated brine (10 mL). After drying the chloroform extract with anhydrous Na₂SO₄, filtering, concentrating, and drying overnight under vacuum at 40° C., the product (240 mg, 86% yield) was isolated as a yellow solid.

Example 4

Oxidation Dearomatization—Trial 4

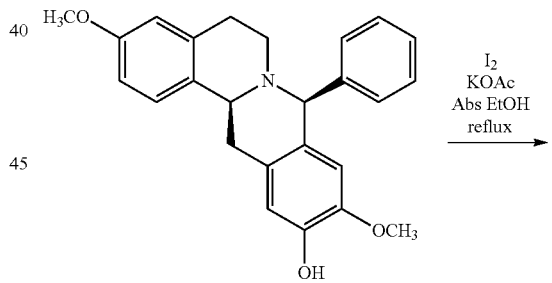

Chemical Formula: C₂₅H₂₅NO₃
Exact Mass: 387.18
Molecular Weight: 387.48

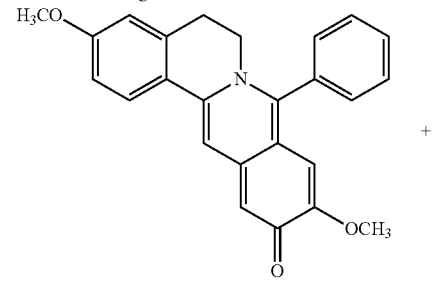

Chemical Formula: C₂₅H₂₁NO₃
Exact Mass: 383.15
Molecular Weight: 383.45

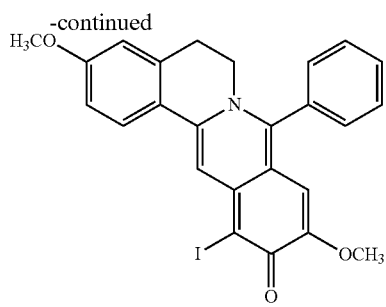

Chemical Formula: C$_{25}$H$_{20}$INO$_3$
Exact Mass: 509.05
Molecular Weight: 509.34

Into a 3 necked round bottom flask was charged the berbine (340 mg, 0.88 mmol), potassium acetate (4.0 eq., 345 mg, 3.51 mmol) and absolute ethanol (25 mL). Into the reaction mixture was added iodine (2.0 eq., 440 mg, 6.40 mmol). The reaction mixture was refluxed for 18 hr and then cooled to room temperature. Ethanol was then removed under reduced pressure leaving dark oil. To the oil was added distilled water (50 mL) and 10% aqueous sodium thiosulfate (20 mL). This solution was stirred for 30 minutes at room temperature where a yellow solid formed. The solid was filtered, washed with 10% sodium thiosulfate (10 mL) and distilled water (2×20 mL). The solid was dried on the funnel and them under reduced pressure for 24 hr at 40° C. yielding a mixture of products (320 mg, 96% MW: 383, 4% MW: 509).

Example 5

Oxidation Dearomatization—Trial 5

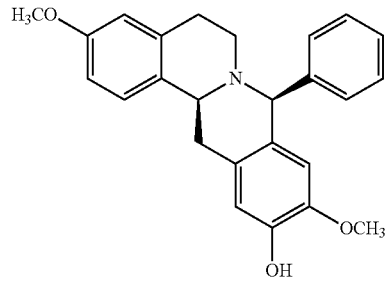

Chemical Formula: C$_{25}$H$_{25}$NO$_3$
Exact Mass: 387.18
Molecular Weight: 387.48

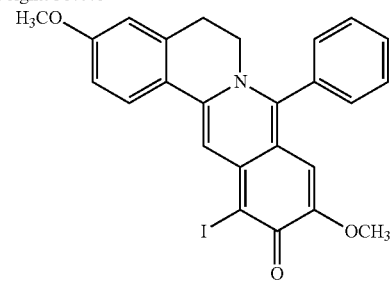

Chemical Formula: C$_{25}$H$_{20}$INO$_3$
Exact Mass: 509.05
Molecular Weight: 509.34

Into a 3 necked round bottom flask was charged the berbine (170 mg, 0.44 mmol), potassium acetate (4.0 eq., 170 mg, 1.75 mmol) and absolute ethanol (20 mL). Into the reaction mixture was added iodine (4.0 eq., 445 mg, 1.70 mmol). The reaction mixture was refluxed for 18 hr and then stirred at room temperature for 24 hr. At this time, the reaction was deemed complete by HPLC, and a small amount precipitate was present. The precipitate was filtered and the filtrate was transferred into a single necked round bottom flask. The solvent was evaporated under reduced pressure and then the residue was dissolved in CHCl$_3$ (50 mL). The chloroform solution was washed with 10% aqueous sodium thiosulfate (2×25 mL) and then dried over anhydrous sodium sulfate. After filtration to remove the sodium sulfate and evaporation of the chloroform, the crude product (250 mg) was isolated as an oil. Purification of the product was accomplished using preparative HPLC using a gradient elution from 0% i-PrOH/CHCl$_3$ to 5% i-PrOH/CHCl$_3$. Similar fractions were combined, and then evaporated yielding the product (190 mg, 85% yield) as a yellow crystalline solid after drying under vacuum overnight at room temperature.

Example 6

Oxidation Dearomatization—Trial 6

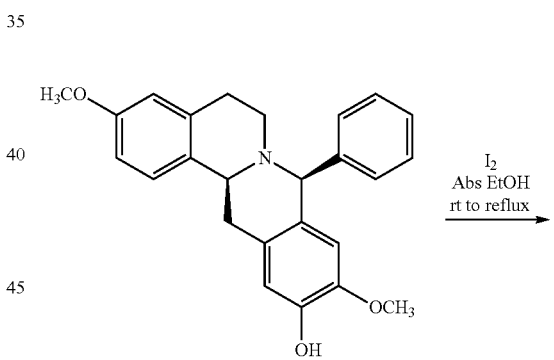

Chemical Formula: C$_{25}$H$_{25}$NO$_3$
Exact Mass: 387.18
Molecular Weight: 387.48

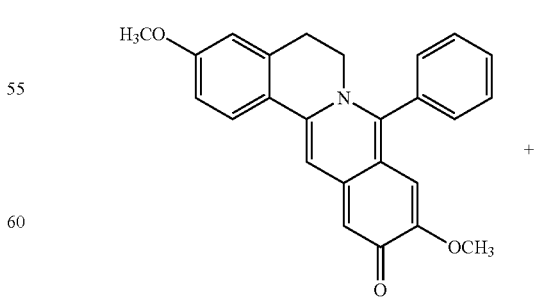

Chemical Formula: C$_{25}$H$_{21}$NO$_3$
Exact Mass: 383.15
Molecular Weight: 383.45

-continued

Chemical Formula: C$_{25}$H$_{20}$INO$_3$
Exact Mass: 509.05
Molecular Weight: 509.34

Into a 3 necked round bottom flask was charged the berbine (270 mg, 0.70 mmol) and absolute ethanol (10 mL). To this mixture was added iodine (2.0 eq, 350 mg, 1.39 mmol) and this mixture was stirred at room temperature for 72 hr, and then refluxed for 24 hr, at which time the reaction was deemed complete by HPLC. To the reaction mixture was added absolute ethanol (20 mL) and stirred for 24 hr wherein a precipitate formed. The yellow precipitate was isolated by filtration. The precipitate was washed with distilled water (10 mL), 10% aqueous sodium thiosulfate (20 mL), and distilled water (10 mL). After drying on the funnel, the yellow solid was dried further in the vacuum oven at 40° C. yielding a mixture of products (280 mg, 58% MW: 383, 42% MW: 509).

Example 7

Oxidation Dearomatization—Trial 7

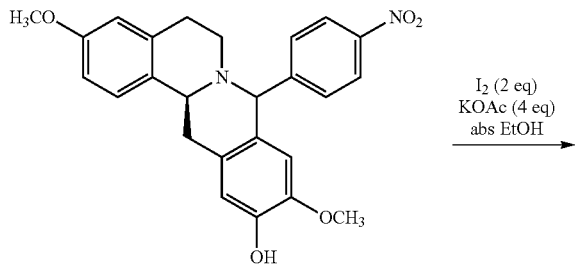

Chemical Formula: C$_{25}$H$_{24}$N$_2$O$_5$
Exact Mass: 432.17
Molecular Weight: 432.48

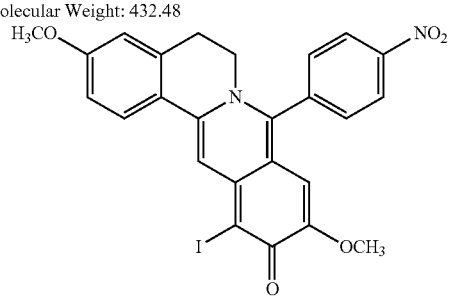

Chemical Formula: C$_{25}$H$_{19}$IN$_2$O$_5$
Exact Mass: 554.03
Molecular Weight: 554.34

Into a 3 necked round bottom flask was charged the berbine (620 mg, 1.43 mmol), potassium acetate (4.0 eq.; 560 mg, 5.72 mmol) and absolute ethanol (50 mL). To this mixture was added iodine (2.0 eq, 727 mg, 2.86 mmol) and this mixture was stirred at room temperature for 72 hr, then refluxed for 24 hr at which time the reaction was deemed complete by HPLC. The yellow precipitate was isolated by filtration. The precipitate was washed with absolute ethanol (5.0 mL), 10% aqueous sodium thiosulfate (10 mL), and distilled water (10 mL). After drying on the funnel, the solid was dried further in the vacuum oven at room temperature yielding the product (310 mg, 39% yield).

Example 8

Oxidation Dearomatization—Trial 8

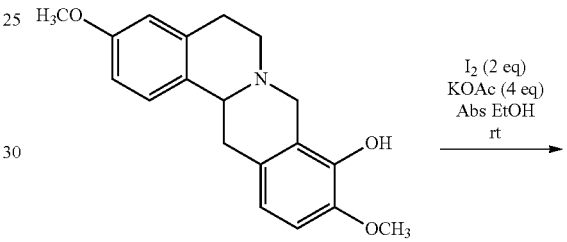

Chemical Formula: C$_{19}$H$_{21}$NO$_3$
Exact Mass: 311.15
Molecular Weight: 311.38

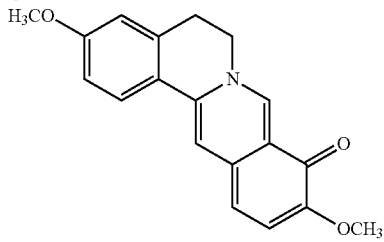

Chemical Formula: C$_{19}$H$_{17}$NO$_3$
Exact Mass: 307.12
Molecular Weight: 307.35

Into a 3 necked round bottom flask was charged the berbine (110 mg, 0.35 mmol), potassium acetate (4.0 eq., 140 mg, 1.41 mmol) and absolute ethanol (10 mL). Into the reaction mixture was added iodine (2.0 eq., 177 mg, 0.70 mmol). The reaction mixture was stirred at room temperature for 72 hr then refluxed for an additional 24 hr. At this time, the reaction was deemed complete by HPLC. The solvent was evaporated under reduced pressure and the residue was dissolved in CHCl$_3$ (50 mL). The chloroform solution was washed with distilled water (20 mL), 10% aqueous sodium thiosulfate (2×25 mL) and then dried over anhydrous sodium sulfate. After filtration to remove the sodium sulfate and evaporation of the chloroform, the product (100 mg, 93% yield) was isolated as an oil.

Example 9

Oxidation Dearomatization—Trial 9

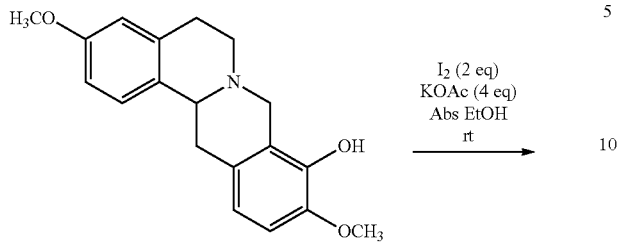

Chemical Formula: $C_{19}H_{21}NO_3$
Exact Mass: 311.15
Molecular Weight: 311.38

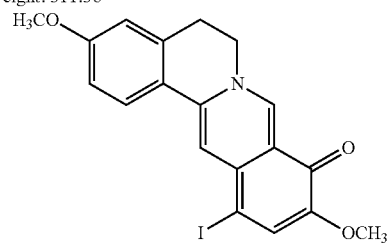

Chemical Formula: $C_{19}H_{16}INO_3$
Exact Mass: 433.02
Molecular Weight: 433.25

Into a 3 necked round bottom flask was charged the berbine (140 mg, 0.45 mmol), potassium acetate (4.0 eq., 180 mg, 1.80 mmol) and absolute ethanol (15 mL). Into the reaction mixture was added iodine (2.0 eq., 228 mg, 0.90 mmol). The reaction mixture was stirred at room temperature for 18 hr. At this time, the reaction was deemed complete by HPLC. After filtering the reaction mixture through a sintered glass funnel, the filtrate was evaporated under reduced pressure. To the residue was added distilled water (20 mL). $CHCl_3$ (25 mL) was added and the mixture was transferred to a separatory funnel. The aqueous was extracted with $CHCl_3$ (2×25 mL). The chloroform extracts were combined, washed with 10% aqueous sodium thiosulfate (2×25 mL) and then dried over anhydrous sodium sulfate. After filtration to remove the sodium sulfate and evaporation of the chloroform, the product (150 mg, 77% yield) was isolated as an oil.

Example 10

Oxidation Dearomatization—Trial 10

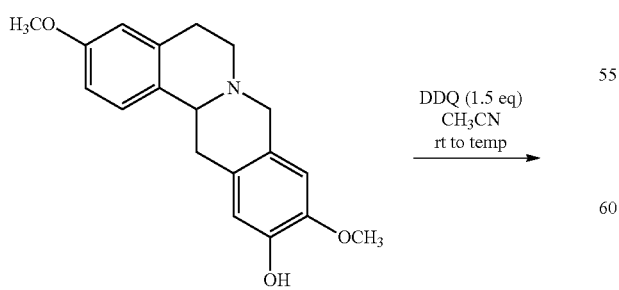

Chemical Formula: $C_{19}H_{21}NO_3$
Exact Mass: 311.15
Molecular Weight: 311.38

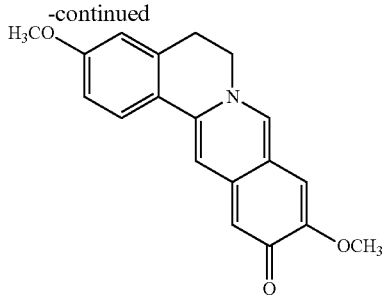

Chemical Formula: $C_{19}H_{17}NO_3$
Exact Mass: 307.12
Molecular Weight: 307.35

Into a 3 necked round bottom flask was charged the berbine (180 mg, 0.58 mmol) and anhydrous acetonitrile (10 mL). Into the reaction mixture was added DDQ: 2,3-dichloro-5,6-dicyano-p-benzoquinone (1.5 eq., 197 mg, 0.87 mmol). The reaction mixture was stirred at room temperature for 18 hr. At this time, an additional amount of DDQ (100 mg, 0.44 mmol) and anhydrous acetonitrile (10 mL) was added. After stirring for an additional 24 hr the reaction was deemed complete by HPLC. At this time, saturated $K_2CO_3$ (5.0 mL) was added and this mixture was stirred for 1 hr. Distilled water (10 mL) was added and the mixture was extracted with $CHCl_3$ (3×20 mL). The chloroform extracts were combined, and then dried over anhydrous sodium sulfate. After filtration to remove the sodium sulfate and evaporation of the chloroform, the product (170 mg, 95% yield) was isolated as an oil after drying under vacuum for 24 hr at 40° C.

Example 11

Oxidation Dearomatization—Trial 11

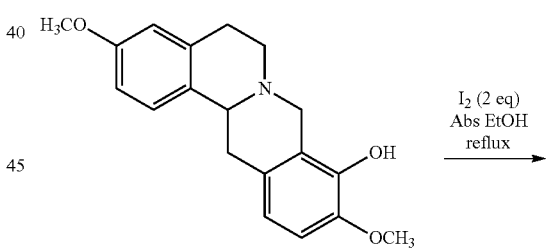

Chemical Formula: $C_{19}H_{21}NO_3$
Exact Mass: 311.15
Molecular Weight: 311.38

Chemical Formula: $C_{19}H_{17}NO_3$
Exact Mass: 307.12
Molecular Weight: 307.35

Into a 3 necked round bottom flask was charged the berbine (120 mg, 0.39 mmol) and absolute ethanol (15 mL). Into the reaction mixture was added iodine (2.0 eq., 195 mg, 0.77 mmol). The reaction mixture was refluxed for 24 hr. At this time, the reaction was deemed complete by HPLC. The reaction mixture was transferred to a single necked flask and was then evaporated under reduced pressure. To the residue was added $CHCl_3$ (50 mL) and the mixture was transferred to a separatory funnel. The chloroform extract was washed with 10% aqueous sodium thiosulfate (2×25 mL), distilled water (20 mL), and then dried over anhydrous sodium sulfate. After filtration to remove the sodium sulfate and evaporation of the chloroform, the product (100 mg, 84% yield) was isolated as an oil.

What is claimed is:

1. A compound of Formula (VIIIa), Formula (VIIIb), or a pharmaceutically acceptable salt thereof:

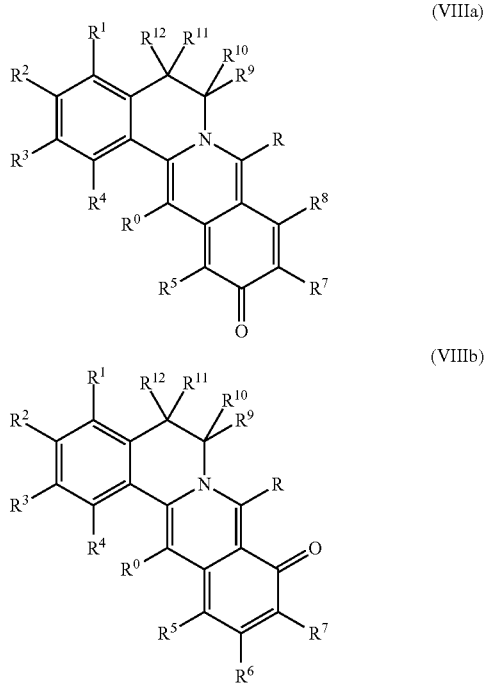

wherein:
R is hydrocarbyl or substituted hydrocarbyl;
$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form {—}O(CH$_2$)$_n$O{—};
$R^5$, $R^6$, when present, $R^7$, and $R^8$, when present, independently are hydrogen, halogen, $OR^{15}$, $NO_2$, $NR^{15}R^{16}$, cyano, thiol, hydrocarbyl, or substituted hydrocarbyl;
$R^0$, $R^9$, $R^{10}$, $R^{11}$, and $R^{12}$ independently are hydrogen, halogen, hydrocarbyl, or substituted hydrocarbyl;
$R^{15}$ and $R^{16}$ independently are hydrogen, hydrocarbyl, or substituted hydrocarbyl; and
n is an integer from 1 to 3.

2. The compound of claim 1, wherein R is alkyl, substituted alkyl, alkenyl, substituted alkenyl, aryl, or substituted aryl; $R^1$, $R^2$, $R^3$, and $R^4$ independently are hydrogen, halogen, $OR^{15}$, $NO_2$, $NR^{15}R^{16}$, or together $R^2$ and $R^3$ form {—}O(CH$_2$)$_n$O{—}; $R^0$, $R^9$, $R^{10}$, $R^{11}$, and $R^{12}$ independently are hydrogen, halogen, alkyl, substituted alkyl, alkenyl, substituted alkenyl, aryl, or substituted aryl; $R^5$, $R^6$, when present, $R^7$, and $R^8$, when present, independently are hydrogen, halogen, $OR^{15}$, $NO_2$, or $NR^{15}R^{16}$; and $R^{15}$ and $R^{16}$ independently are hydrogen, alkyl, substituted alkyl, alkenyl, substituted alkenyl, aryl, or substituted aryl.

3. The compound of claim 2, wherein each of $R^0$, $R^1$, $R^4$, $R^9$, $R^{10}$, $R^{11}$, and $R^{12}$ is hydrogen; $R^2$ and $R^3$ independently are hydrogen, halogen, hydroxy, $C_1$-$C_6$ alkoxy, aryloxy, amine, amino, nitro, or together $R^2$ and $R^3$ form {—}O(CH$_2$)$_n$O{—}; and $R^5$, $R^6$, when present, $R^7$, and $R^8$, when present, independently are hydrogen, halogen, hydroxy, $C_1$-$C_6$ alkoxy, aryloxy, amine, amino, or nitro.

4. The compound of claim 3, wherein $R^2$ is hydroxy or $C_1$-$C_6$ alkoxy and $R^3$ is hydrogen, or together $R^2$ and $R^3$ form {—}O(CH$_2$)O{—}.

5. The compound of claim 4, wherein R is alkyl, substituted alkyl, cycloalkyl, substituted cycloalkyl, aryl, or substituted aryl.

6. A composition comprising one of the compounds of claim 1 and at least one pharmaceutically acceptable excipient.

7. A process for preparing a compound of Formula (VIIIa) or Formula (VIIIb), the process comprising either step a) or step b):
a) contacting a compound of Formula (VIIa) with an oxidizing agent to form the compound of Formula (VIIIa) according to the following reaction scheme:

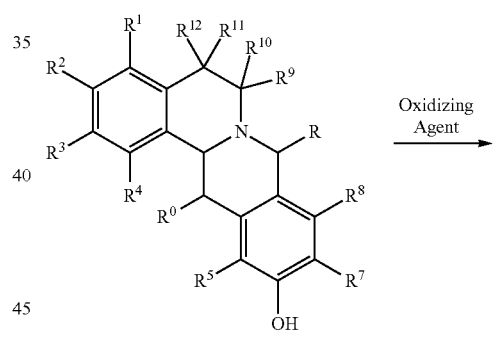

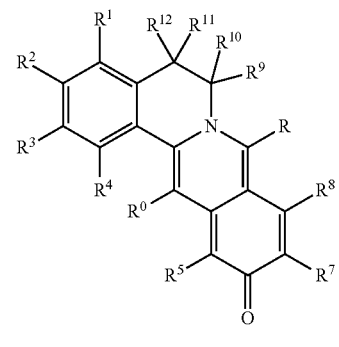

or b) contacting a compound of Formula (VIIb) with an oxidizing agent to form the compound of Formula (VIIIb) according to the following reaction scheme:

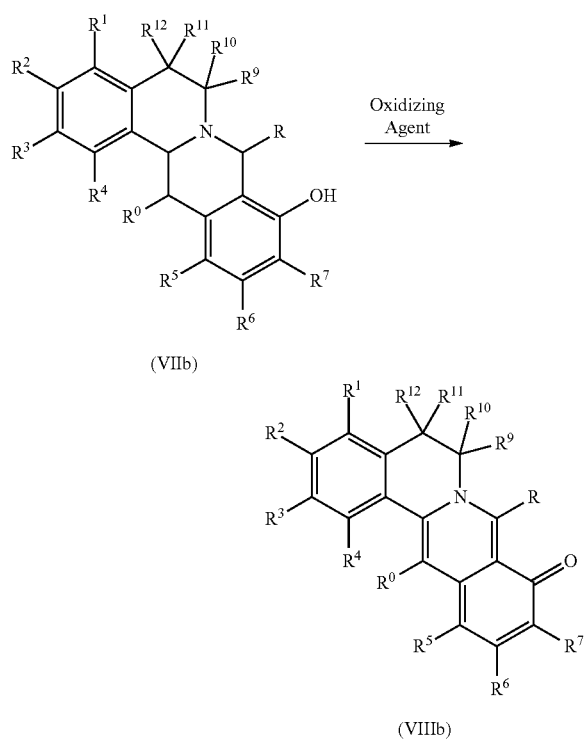

(VIIb)

(VIIIb)

wherein:

R is hydrocarbyl or substituted hydrocarbyl;

$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form $\{-\}O(CH_2)_nO\{-\}$;

$R^5$, $R^6$, when present, $R^7$, and $R^8$, when present, independently are hydrogen, halogen, $OR^{15}$, $NO_2$, $NR^{15}R^{16}$, cyano, thiol, hydrocarbyl, or substituted hydrocarbyl;

$R^0$, $R^9$, $R^{10}$, $R^{11}$, and $R^{12}$ independently are hydrogen, halogen, hydrocarbyl, or substituted hydrocarbyl;

$R^{15}$ and $R^{16}$ independently are hydrogen, hydrocarbyl, or substituted hydrocarbyl;

n is an integer from 1 to 3; and wherein each of $R^1$, $R^2$, $R^3$, $R^4$, $R^5$, $R^6$, when present, $R^7$, and $R^8$, when present, is other than hydroxy.

8. The process of claim 7, wherein R is alkyl, substituted alkyl, alkenyl, substituted alkenyl, aryl, or substituted aryl; $R^1$, $R^2$, $R^3$, and $R^4$ independently are hydrogen, halogen, $OR^{15}$, $NO_2$, $NR^{15}R^{16}$, or together $R^2$ and $R^3$ form $\{-\}O(CH_2)_nO\{-\}$; $R^0$, $R^9$, $R^{10}$, $R^{11}$, and $R^{12}$ independently are hydrogen, halogen, alkyl, substituted alkyl, alkenyl, substituted alkenyl, aryl, or substituted aryl; $R^5$, $R^6$, when present, $R^7$, and $R^8$, when present, independently are hydrogen, halogen, $OR^{15}$, $NO_2$, or $NR^{15}R^{16}$; and $R^{15}$ and $R^{16}$ independently are hydrogen, alkyl, substituted alkyl, alkenyl, substituted alkenyl, aryl, or substituted aryl.

9. The process of claim 8, wherein each of $R^0$, $R^1$, $R^4$, $R^9$, $R^{10}$, $R^{11}$, and $R^{12}$ is hydrogen; $R^2$ and $R^3$ independently are hydrogen, halogen, hydroxy, $C_1$-$C_6$ alkoxy, aryloxy, amine, amino, nitro, or together $R^2$ and $R^3$ form $\{-\}O(CH_2)_nO\{-\}$; and $R^5$, $R^6$, when present, $R^7$, and $R^8$, when present, independently are hydrogen, halogen, hydroxy, $C_1$-$C_6$ alkoxy, aryloxy, amine, amino, or nitro.

10. The process of claim 9, wherein R is alkyl, substituted alkyl, cycloalkyl, substituted cycloalkyl, aryl, or substituted aryl; $R^2$ is hydroxy or $C_1$-$C_6$ alkoxy and $R^3$ is hydrogen, or together $R^2$ and $R^3$ form $\{-\}O(CH_2)O\{-\}$; $R^5$ is hydrogen or halogen; $R^6$, when present, is hydrogen, $R^7$ is hydroxy or $C_1$-$C_6$ alkoxy; and $R^8$, when present, is hydrogen.

11. The process of claim 7, wherein the oxidizing agent is a halogen or a quinone; the mole to mole ratio of the compound of Formula (VIIa) or Formula (VIIb) to the oxidizing agent is from about 1:1 to about 1:10; and the contacting is conducted at a temperature from about −50° C. to about 200° C.

12. The process of claim 7, wherein the contacting is conducted in the presence of a non-oxidizable solvent; and the volume to mass ratio of the solvent to the compound of Formula (VIIa) or Formula (VIIb) is from about 10:1 to about 300:1.

13. The process of claim 7, wherein the contacting is conducted in the presence of proton acceptor chosen from an acetate salt, a bicarbonate salt; a borate salt, a carbonate salt, a hydroxide salt, a phosphate salt, a butoxide, an organic base, or a combination thereof; and the mole to mole ratio of the compound of Formula (VIIa) or Formula (VIIb) to the proton acceptor is from about 1:1 to about 1:10.

14. The process of claim 11, wherein the contacting is conducted in the presence of a solvent chosen from an alcohol or acetonitrile; and the volume to mass ratio of the solvent to the compound of Formula (VIIa) or Formula (VIIb) is from about 50:1 to about 250:1.

15. The process of claim 14, wherein the contacting is conducted in the presence of an acetate salt; and the mole to mole ratio of the compound of Formula (VIIa) or Formula (VIIb) to the acetate salt is from about 1:3 to about 1:7.

16. A method for inhibiting the growth of a cancer cell, the method comprising contacting the cancer cell with an effective amount of a compound of Formula (VIIIa), Formula (VIIIb), or a pharmaceutically acceptable salt thereof:

(VIIIa)

(VIIIb)

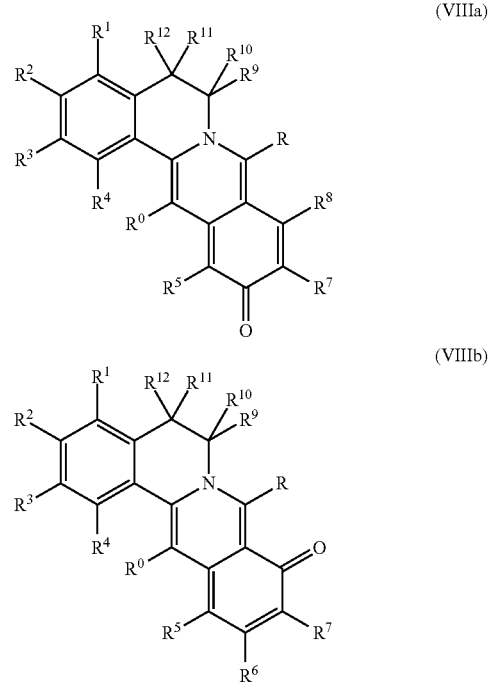

wherein:

R is hydrocarbyl or substituted hydrocarbyl;

$R^1$, $R^2$, $R^3$, and $R^4$ independently are hydrogen, halogen, $OR^{15}$, $NO_2$, $NR^{15}R^{16}$, cyano, thiol, hydrocarbyl, substituted hydrocarbyl, or together $R^2$ and $R^3$ form $\{-\}O(CH_2)_nO\{-\}$;

$R^5$, $R^6$, when present, $R^7$, and $R^8$, when present, independently are hydrogen, halogen, $OR^{15}$, $NO_2$, $NR^{15}R^{16}$, cyano, thiol, hydrocarbyl, or substituted hydrocarbyl;

$R^0$, $R^9$, $R^{10}$, $R^{11}$, and $R^{12}$ independently are hydrogen, halogen, hydrocarbyl, or substituted hydrocarbyl;

$R^{15}$ and $R^{16}$ independently are hydrogen, hydrocarbyl, or substituted hydrocarbyl; and n is an integer from 1 to 3.

17. The method of claim 16, wherein R is alkyl, substituted alkyl, alkenyl, substituted alkenyl, aryl, or substituted aryl; $R^1$, $R^2$, $R^3$, and $R^4$ independently are hydrogen, halogen, $OR^{15}$, $NO_2$, $NR^{15}R^{16}$, or together $R^2$ and $R^3$ form $\{-\}O(CH_2)_nO\{-\}$; $R^0$, $R^9$, $R^{10}$, $R^{11}$, and $R^{12}$ independently are hydrogen, halogen, alkyl, substituted alkyl, alkenyl, substituted alkenyl, aryl, or substituted aryl; $R^5$, $R^6$, when present, $R^7$, and $R^8$, when present, independently are hydrogen, halogen, $OR^{15}$, $NO_2$, or $NR^{15}R^{16}$; and $R^{15}$ and $R^{16}$ independently are hydrogen, alkyl, substituted alkyl, alkenyl, substituted alkenyl, aryl, or substituted aryl.

18. The method of claim 17, wherein each of $R^0$, $R^1$, $R^4$, $R^9$, $R^{10}$, $R^{11}$, and $R^{12}$ is hydrogen; $R^2$ and $R^3$ independently are hydrogen, halogen, hydroxy, $C_1$-$C_6$ alkoxy, aryloxy, amine, amino, nitro, or together $R^2$ and $R^3$ form $\{-\}O(CH_2)_nO\{-\}$; and $R^5$, $R^6$, when present, $R^7$, and $R^8$, when present, independently are hydrogen, halogen, hydroxy, $C_1$-$C_6$ alkoxy, aryloxy, amine, amino, or nitro.

19. The method of claim 18, wherein R is alkyl, substituted alkyl, cycloalkyl, substituted cycloalkyl, aryl, or substituted aryl; $R^2$ is hydroxy or $C_1$-$C_6$ alkoxy and $R^3$ is hydrogen, or together $R^2$ and $R^3$ form $\{-\}O(CH_2)O\{-\}$; $R^5$ is hydrogen or halogen; $R^6$, when present, is hydrogen, $R^7$ is hydroxy or $C_1$-$C_6$ alkoxy; and $R^8$, when present, is hydrogen.

20. The method of claim 16, wherein the cancer cell is in vitro.

* * * * *